US006534965B2

United States Patent
Ueno et al.

(10) Patent No.: US 6,534,965 B2
(45) Date of Patent: Mar. 18, 2003

(54) PARTICLE SIGNAL PROCESSING APPARATUS AND PARTICLE MEASUREMENT APPARATUS USING SAME

(75) Inventors: Kunio Ueno, Kakogawa (JP); Seiya Shinabe, Kobe (JP); Yoichi Nakamura, Kobe (JP)

(73) Assignee: Sysmex Corporation, Hyogo (JP)

(*) Notice: Subject to any disclaimer, the term of this patent is extended or adjusted under 35 U.S.C. 154(b) by 0 days.

(21) Appl. No.: 09/813,833

(22) Filed: Mar. 22, 2001

(65) Prior Publication Data

US 2001/0032495 A1 Oct. 25, 2001

(30) Foreign Application Priority Data

Apr. 21, 2000 (JP) .......................................... 2000-120373

(51) Int. Cl.[7] .............................................. G01N 72/00
(52) U.S. Cl. ..................................... 324/71.4; 324/71.1
(58) Field of Search ................................ 324/71.4, 71.1, 324/71.3, 454, 691, 692, 693, 713; 436/63; 73/865.5; 702/26

(56) References Cited

U.S. PATENT DOCUMENTS 4,277,743 A * 7/1981 Guggenbuhl ............... 324/71.1
4,714,890 A * 12/1987 Dechene et al. ............ 324/454
5,130,639 A * 7/1992 Hachey ...................... 324/444

\* cited by examiner

Primary Examiner—N. Le
Assistant Examiner—James Kerveros
(74) Attorney, Agent, or Firm—Birch, Stewart, Kolasch & Birch, LLP

(57) ABSTRACT

A particle signal processing apparatus which processes a particle signal representative of characteristics of particles includes an amplifier having input and output terminals for amplifying a particle signal including serial pulses to output an output signal including the amplified serial pulses, a filter section for extracting a low frequency component from the output signal of the amplifier so that the extracted component is fed back into the input terminal as a negative feedback signal, and a feedback signal control section for allowing the filter section to fix the negative feedback signal when each of the amplified pulses rises and to hold the fixed negative feedback signal while the amplified pulse is larger than a threshold value.

6 Claims, 3 Drawing Sheets

PARTICLE SIGNAL PROCESSING APPARATUS AND PARTICLE MEASUREMENT APPARATUS USING SAME

CROSS-REFERENCE TO RELATED APPLICATION

This application is related to Japanese Patent Application No. 2000-120373 filed on Apr. 21, 2000, whose priority is claimed under 35 USC § 119, the disclosure of which is incorporated by reference in its entirety.

BACKGROUND OF THE INVENTION

1. Field of the Invention

The present invention relates to a particle signal processing apparatus and a particle measurement apparatus using the same, such apparatuses being used for measurement of particles in body fluid and industrial particles.

2. Description of the Related Art

Conventionally, particle measurement apparatuses of the electric measurement type are provided with two chambers that communicate with each other through a micro through hole (orifice) and it is so arranged that when a particle-contained solution flows from one chamber to the other, a pulse-formed electric resistance change is detected as a particle signal each time a particle passes through the orifice. Since it is known that a peak value of the particle signal is proportional to a volume of the particle, the particle signal is utilized in calculating a particle diameter or in sorting out particles.

But problems with such particle signal measurement apparatuses are that if bubbles contained in the particle-contained solution are present near the micro through hole, the obtained particle signal (pulse signal) fluctuates with respect to a base line (low frequency fluctuation) and it is difficult to determine the peak value of the particle signal accurately.

SUMMARY OF THE INVENTION

In view of the prior art described above, it is an object of the present invention to provide a particle measurement apparatus in which a base line of a particle signal including serial pulses is stabilized to determine a peak value of each pulse signal accurately and which permits measurement of particles with precision.

The object of the present invention is achieved by providing a particle signal processing apparatus which processes a particle signal representative of characteristics of particles, comprising: an amplifier having input and output terminals for amplifying a particle signal including serial pulses to output an output signal including the amplified serial pulses; a filter section for extracting a low frequency component from the output signal of the amplifier so that the extracted component is fed back into the input terminal as a negative feedback signal; a feedback signal control section for allowing the filter section to fix the negative feedback signal when each of the amplified pulses rises and to hold the fixed negative feedback signal while the amplified pulse is larger than a threshold value.

BRIEF DESCRIPTION OF THE DRAWINGS

A preferred embodiment of the present invention will be illustrated, and not by way of limitation, in conjunction with the accompanying drawings, in which.

DESCRIPTION OF THE PREFERRED EMBODIMENTS

The object particles to be determined in the present invention include a toner, graphite, silica, abrasive material, ceramic powder, pigment, powder paint, cultured cell, blood cell, yeast, plankton and magnetic powder. The particle measurement size ranges from submicrons to hundreds of microns in diameter.

The particle signal processing apparatus according to the present invention is mainly applied to an electric resistance-type particle measurement apparatus but is not limited thereto, and may be applied to an optical-type particle measurement apparatus, for example.

A commercial operational amplifier can be used as the amplifier in the particle signal processing apparatus.

The filter section may be composed of a combination of an operational amplifier, a capacitor and a resistor—what is called a RC active filter.

The feedback signal control section may be composed of a comparator for comparing the pulse output from the amplifier with the threshold value and an analog switch that is actuated by an output of the comparator.

In the feedback signal control section, the output of the amplifier may be input to the comparator through a differential circuit. A commercially available comparator and analog switch may be used for the comparator and analog switch.

The particle signal processing apparatus according to the present invention, when used in an electric resistance-type measurement apparatus, may include a flow cell having first and second chambers, an orifice section through which the first and second chambers communicate with each other, first and second electrodes provided in the first and second chambers respectively, and a detection section for detecting a change in impedance between the first and second electrodes as a particle signal.

In this case, the particle measurement apparatus may further include an analysis section for analyzing the particle signal obtained from the particle signal processing apparatus.

A microcomputer or personal computer may be used for the analysis section.

The detection section in the above particle measurement apparatus may be include d.c. power source to supply a constant current between the first and second electrodes and a current/voltage conversion section to convert a change in a current flowing between the first and second electrodes into a voltage.

Figure 1:
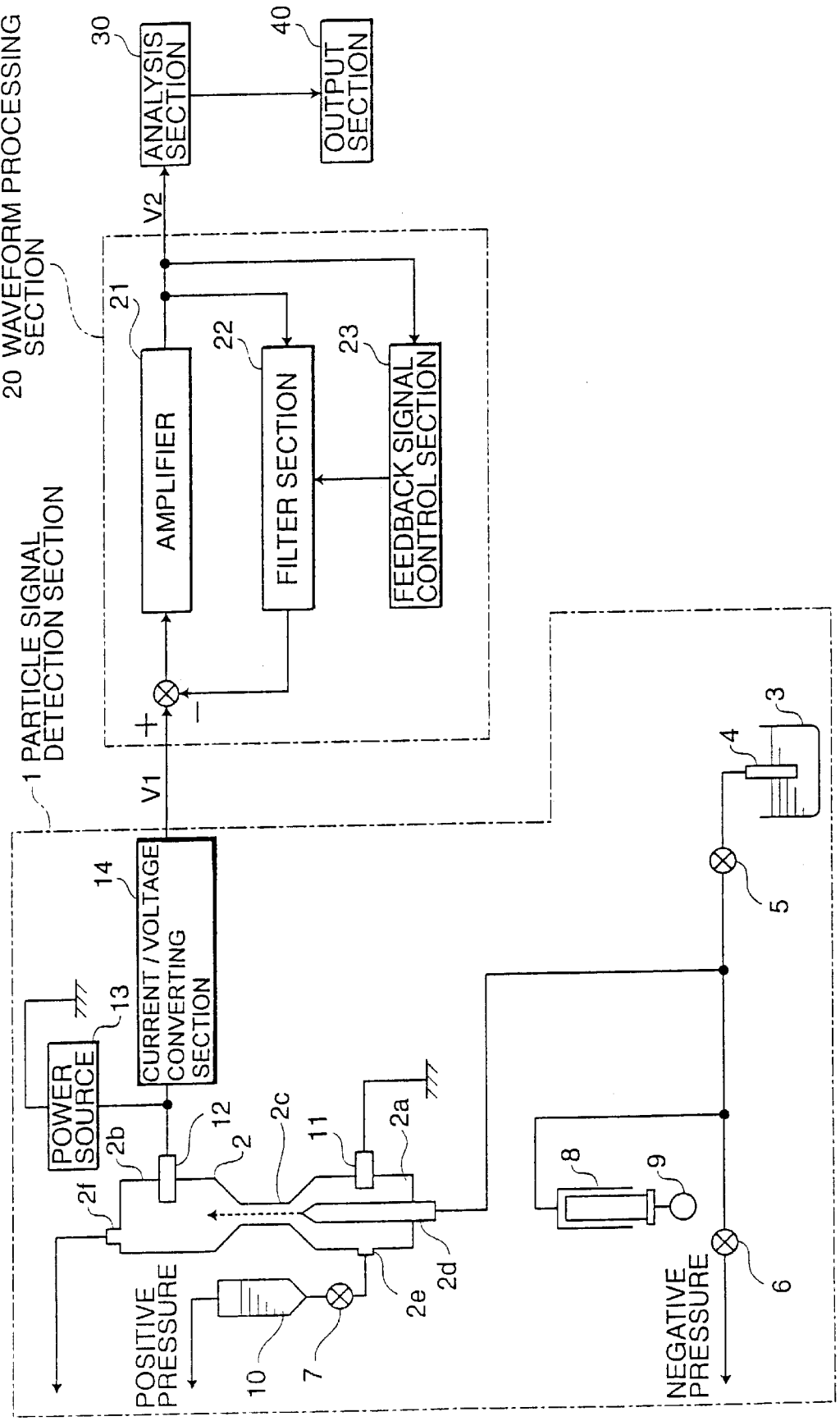
FIG. 1 is a block diagram of a particle measurement apparatus embodying the present invention.

FIG. 1 is a block diagram of a particle measurement apparatus embodying the present invention.

In FIG. 1, a particle signal V1 detected by a particle signal detecting section 1 is processed in waveform in a waveform processing section 20 and output to an analysis section 30 as particle signal V2. On the basis of the particle signal V2, the analysis section 30 counts and sorts out particles and calculates particle volumes and particle diameters. Results are output from an output section 40.

Configuration and Operation of Particle Signal Detection Section

In FIG. 1, the particle signal detection section 1 comprises a flow cell 2, a sample liquid container 3 to hold a sample liquid containing particles to be measured, a suction nozzle 4 for sucking the sample liquid, valves 5, 6, 7, a syringe 8, a motor 9 for driving the syringe 8 and a sheath liquid container 10. The flow cell 2 is composed of a first cell 2a, a second cell 2b, a orifice section 2c in which the first cell 2a communicates with the second cell 2b through a micro through hole (orifice) and a nozzle 2d to jet the sample liquid to the orifice section 2c. In addition, an inlet port 2e to accept the sheath liquid from the container 10 through valve 7 is provided in the first cell 2a, while an outlet port 2f to discharge the sheath liquid and sample liquid is provided in the second cell 2b.

Furthermore, inside the first cell 2a and the second cell 2b are provided electrodes 11, 12, respectively. A d.c. power source 13 is provided to supply a constant current between electrodes 11, 12 through the orifice section 2c.

In such a particle signal detecting section 1, if the valves 5, 6 are first opened for a predetermined period of time, the sample liquid is sucked by the suction nozzle 4 under a negative pressure until a flow path between the valves 5, 6 is filled with the sample liquid. Then, the sample liquid is discharged into the first cell 2a when the syringe 8 presses out the sample liquid between the valves 5, 6 to the sample nozzle 2d at a constant flow rate.

The valve 7 is opened at the same time and thereby the sheath liquid is supplied to the first cell 2a. And the sample liquid is sheathed with the sheath liquid, and further squeezed by the orifice section 2c to form a sheath flow.

In the sheath flow, the particles contained beforehand in the sample liquid are aligned and flowed one by one in a line through the orifice 2c. The sample liquid and the sheath liquid that have passed through the orifice 2c are discharged through the outlet port 2f of the second cell 2b.

An electric resistance or impedance between the electrodes 11 and 12 is determined by a conductivity (electrical conductivity) of the sheath liquid, an orifice size (sectional area) of the orifice section 2c, an electrical conductivity of the sample liquid and a diameter of the sheath flow of the sample liquid.

Meanwhile, as mentioned above, the constant current is supplied between the electrode 12 and the electrode 11 from the d.c. power source 13. If a particle passes through the orifice section 2c, the electric resistance at both ends of the orifice section 2c changes. Therefore, the current that flows between the electrode 12 and the electrode 11 changes in the form of pulse every time one particle passes. The maximum value of change (pulse height) is proportional with the size of the particle passing through the orifice section 2c. This change in the current is converted into a voltage by a current/voltage converting section 14 and outputted as the particle signal V1. In this way, the particle signal detecting section 1 generates the particle signal V1.

Figure 2:
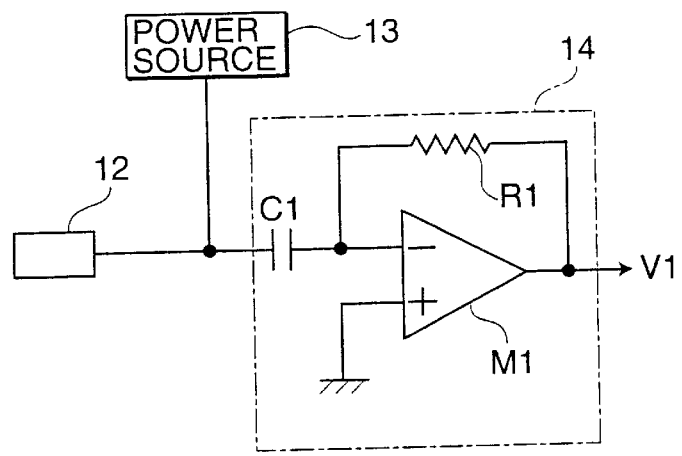
FIG. 2 is a detailed connection diagram of an essential part of the embodiment of the present invention.

By the way, the current/voltage converting section 14 can be formed of a condenser C1, an operational amplifier M1 and a resistor R1 as shown in FIG. 2.

Configuration and Operation of Waveform Processing Section

The waveform processing section 20 shown in FIG. 1 includes an amplifier 21 to amplify the particle signal V1 by a suitable degree of amplitude, a filter section 22 acting as a negative feedback element to extract a low frequency component from an output of the amplifier 21 as a feedback signal to be fed back into an input of the amplifier 21 and a feedback signal control section 23 to allow the filter section 22 to fix and hold the feedback signal from the output of the amplifier 21 while the pulse waveform output from the amplifier 21 is larger than a threshold value.

Figure 3:
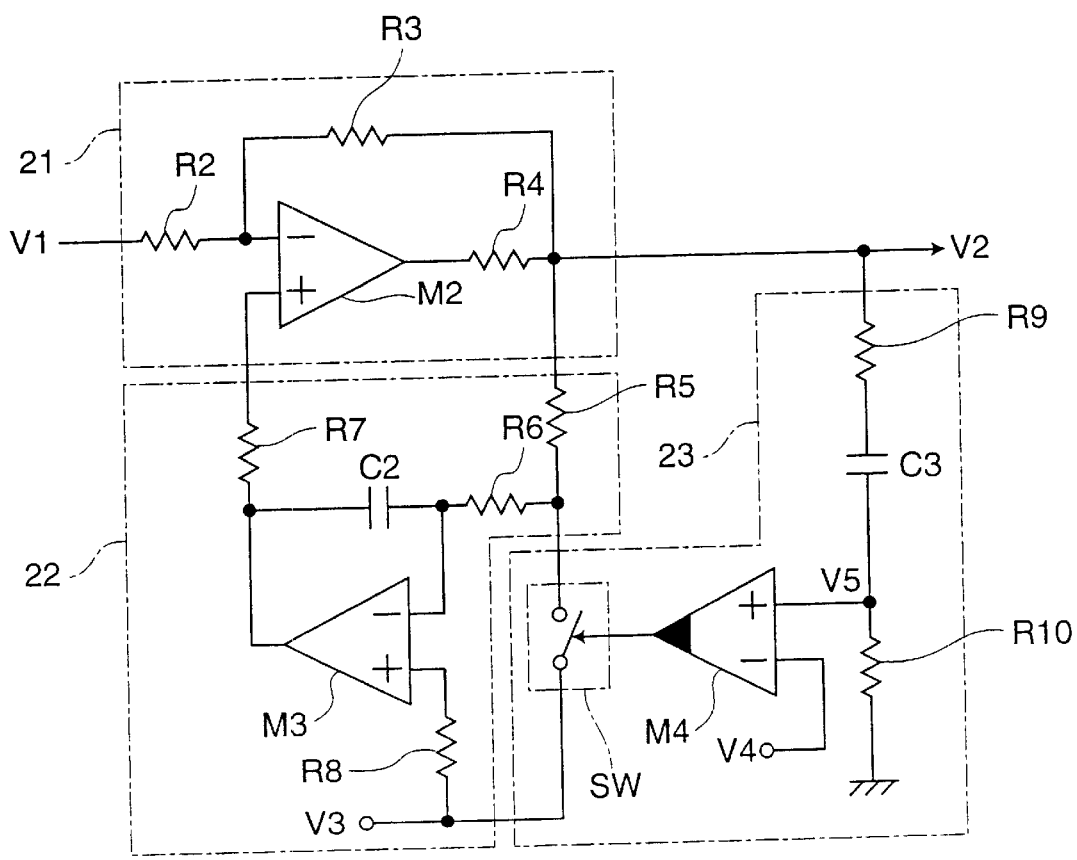
FIG. 3 is a detailed connection diagram of another essential part of the embodiment of the present invention.

FIG. 3 is a detailed connection diagram of the waveform processing section 20. The amplifier 21 is formed of an operational amplifier M2 and resistors R2 to R4. And in the present embodiment, for example, the values of the resistors R2 to R4 are.: so set that the amplifier M2 has a gain of 2.2.

The filter section 22 is provided with an operational amplifier M3, a capacitor C2, resistors R5 to R8 to form an RC active filter. And the values of the capacitor C2 and resistors R5, R6 are so set that the filter section 22 works as a low pass filter with a cutoff frequency of 1 kHz. To a non-reversible input of the operational amplifier M3 is applied with a reference voltage V3, for example, 2 V.

The feedback signal control section 23 is provided with a comparator M4 and a differential circuit composed of an analog switch SW, resistors R9, R10 and a capacitor C3. To the comparator M4, a reference voltage (threshold voltage) V4 is applied. The comparator M4 turns on the analog switch SW when a signal V5 output from the differential circuit is larger than the threshold voltage V4.

As the operational amplifiers M1, M2 and M3 can be used Model LMV 824M made by. National Semiconductor. As the comparator M4 can be used Model LMV331M5 made by National Semiconductor. In case the output needs to be kept low in offset voltage, it is desirable to use an operation amplifier of a low offset voltage as the operational amplifier M3.

The operation of the above described configuration will be explained.

Figure 4:
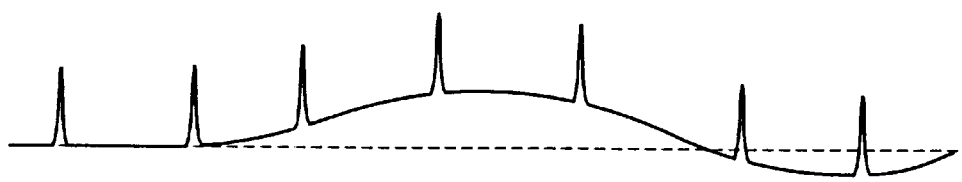
FIG. 4 is a waveform diagram of a particle signal in the embodiment.

A pulse signal having a pulse waveform as shown in FIG. 4 is inputted to the amplifier 21 as the particle signal V1 from the particle signal detecting section 1. The pulse signal shown in FIG. 4 has a low frequency component as shown in FIG. 5, which causes the base line of the pulse waveform in FIG. 4 to fluctuate.

Figure 5:
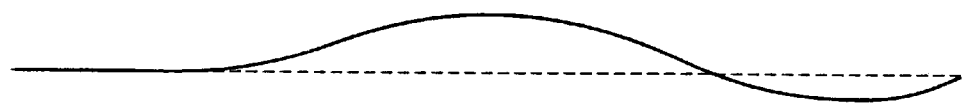
FIG. 5 is a waveform diagram showing the base line in the embodiment.
Figure 6:
FIG. 6 is a waveform diagram of a particle signal processed in the embodiment.

The pulse signal output from the amplifier 21 is filtered through the filter section 22, and the low frequency component shown in FIG. 5 is negatively fed back into the amplifier 21. Therefore, the low frequency component shown in FIG. 5 is removed from the pulse signal shown in FIG. 4, and the output waveform of the amplifier 21 becomes a waveform with a stable base line as shown in FIG. 6.

But it is difficult to sufficiently extract only the low frequency component shown in FIG. 5 from the output of the amplifier 21 by the filter section 22 and a pulse signal component (high frequency component) partially passes the filter section 22 and is negatively fed back into the amplifier 21. That causes the pulse waveform shown in FIG. 6 to strain.

It is the feedback signal control section 23 that is provided to eliminate that strain. In the feedback signal control section 23, the comparator M4 compares the voltage V5, i.e., a differentiated value of the output V2 of the amplifier 21 with the reference voltage V4 and turns on the analog switch SW while the voltage V5 is larger than the voltage V4, that is, only during a period of time corresponding to the pulse width of each pulse contained in the output V2.

When the analog switch SW turns on, the voltage V3 (2V) is applied to two input terminals of the operational amplifier M3 in the filter section 22. Therefore, the filter section 22 does not function as the filter, and the feedback signal is fixed to the voltage just before the analog switch SW is turned on. Thus, because the pulse waveform component is not fed back, an unstrained pulse waveform can be obtained from the amplifier 21.

In the feedback signal control section 23, the output of the amplifier 21 is input to the comparator M4 through the differential circuit composed of the condenser C3 resistors R9, R10. That circuit is provided to quickly detect a rise of the pulse. A detection level of the pulse can be adjusted with the voltage V4 and a differential constant determined by the capacitor C3 and resistors R9, R10.

In case the rise of the pulse is quick enough, the above-mentioned differential circuit may be removed to input the output of the amplifier 21 directly to the comparator M4.

The signal shown in FIG. 6 should be reversed in polarity with respect to the polarity of pulse in FIG. 4 in the present embodiment. But for sake of clarity, an unreversed waveform is shown.

Thus, the particle signal (pulse signal) V2 with a stable base line is inputted into the analysis section 30. Therefore, the analysis section 30 can count the particles from the particle signal V2 and calculates the particle volume and particle size with high precision and outputs them to the output section 40.

According to the present invention, the base line of the particle signal can be stabilized, which permits an accurate measurement of particles on the basis of the particle signal.

Since the feedback is stopped for the pulse corresponding to each particle, the present invention is more effective in preventing the particle signal from straining. In the present invention, the base line is kept from fluctuating and amplifies the particle signal to make good use of the voltage range in the circuit. Especially when the dynamic range of the signal handled is large or the source voltage in the circuit is low, good results can be achieved.

What is claimed is:

1. A particle signal processing apparatus which processes a particle signal representative of characteristics of particles, comprising:

an amplifier having input and output terminals for amplifying a particle signal including serial pulses to output an output signal including the amplified serial pulses;

a filter section for extracting a low frequency component from the output signal of the amplifier so that the extracted component is fed back into the input terminal as a negative feedback signal; and a feedback signal control section for allowing the filter section to fix the negative feedback signal when each of the amplified pulses rises and to hold the fixed negative feedback signal while the amplified pulse is larger than a threshold value.

2. The particle signal processing apparatus of claim 1 wherein the filter section comprises an RC active filter having an operational amplifier, a capacitor and three resistors.

3. The particle signal processing apparatus of claim 1 wherein the feedback signal control section comprises a comparator for comparing each amplified pulse with the threshold value and an analog switch which is actuated by an output signal of the comparator to fix the negative feedback signal output from the filter section.

4. The particle signal processing apparatus of claim 3 wherein each amplified pulse is inputted to the comparator through a differential circuit to emphasize a rise of each amplified pulse.

5. A particle measurement apparatus comprising:

a detection section having a pair of electrodes with an orifice section therebetween for detecting a change in impedance between the electrodes as a particle signal when a liquid containing particles passes through the orifice;

a particle signal processing apparatus which processes a particle signal representative of characteristics of particles, comprising:

an amplifier having input and output terminals for amplifying a particle signal including serial pulses to output an output signal including the amplified serial pulses;

a filter section for extracting a low frequency component from the output signal of the amplifier so that the extracted component is fed back into the input terminal as a negative feedback signal; and a feedback signal control section for allowing the filter section to fix the negative feedback signal when each of the amplified pulses rises and to hold the fixed negative feedback signal while the amplified pulse is larger than a threshold value; and an analysis section for analyzing the particle signal processed by the particle signal processing apparatus.

6. The particle measurement apparatus of claim 5 wherein the detecting section includes a flow cell, a power source and a converting section, the flow cell having first and second chambers, one electrode and the other electrode being positioned in the first and second chambers, respectively, the power source supplying a d.c. current between the pair of electrodes, the converting section converting a current corresponding to the change in impedance into a voltage corresponding to the particle signal.

* * * * *